United States Patent [19]

Vo-Dinh et al.

[11] Patent Number: 5,496,522
[45] Date of Patent: Mar. 5, 1996

[54] BIOSENSOR AND CHEMICAL SENSOR PROBES FOR CALCIUM AND OTHER METAL IONS

[75] Inventors: Tuan Vo-Dinh, Knoxville, Tenn.; Pierre Viallet, Perpignan, France

[73] Assignee: Martin Marietta Energy Systems, Inc., Oak Ridge, Tenn.

[21] Appl. No.: 192,429

[22] Filed: Feb. 7, 1994

[51] Int. Cl.⁶ .................................................. G01N 21/00
[52] U.S. Cl. ................... 422/82.05; 422/82.07; 422/82.08; 436/79; 549/352
[58] Field of Search .......................... 422/82.05, 82.06, 422/82.07, 82.08; 128/634; 356/39; 436/79, 805; 549/352

[56] References Cited

U.S. PATENT DOCUMENTS

| | | | |
|---|---|---|---|
| 4,851,195 | 7/1989 | Matthews et al. | 422/68 |
| 4,861,727 | 8/1989 | Hauenstein et al. | 436/136 |
| 4,974,929 | 12/1990 | Curry | 350/96.29 |
| 5,093,266 | 3/1992 | Leader et al. | 436/68 |
| 5,118,405 | 6/1992 | Kaneko et al. | 204/433 |
| 5,154,890 | 10/1992 | Mauze et al. | 422/82.07 |
| 5,176,882 | 1/1993 | Gray et al. | 422/82.07 |
| 5,190,729 | 3/1993 | Hauenstein et al. | 422/91 |
| 5,194,393 | 3/1993 | Hugl et al. | 436/525 |
| 5,227,134 | 7/1983 | Janata | 422/82.08 |

OTHER PUBLICATIONS

R. Y. Tsien, "New Calcium Indicators and Buffers with High Selectivity Against Mg and Protons" Biochemistry, 19, 2396 1980.

*Primary Examiner*—David A. Redding
*Attorney, Agent, or Firm*—B. E. Harang; I. L. Ericson; J. A. Marasco

[57] ABSTRACT

The present invention relates to chemical sensor and biosensor probes for measuring low concentration of metals and metal ions in complex samples such as biological fluids, living cells, and environmental samples. More particularly the present invention relates to a gel-based Indo-1 and Fura-2 chemical sensor probes for the measurement of low concentrations of calcium, cadmium, magnesium and the like. Also disclosed is a detector device using the sensors of the present invention.

3 Claims, 10 Drawing Sheets

BIOSENSOR AND CHEMICAL SENSOR PROBES FOR CALCIUM AND OTHER METAL IONS

BACKGROUND OF THE INVENTION

1. Field of the Invention

The United States Government has rights in this invention pursuant to contract no. DE-AC05-840R2 1400 between the United States Department of Energy and Martin Marietta Energy Systems, Inc., and funded by the Office of Health and Environmental Research.

The present invention relates to chemical sensors and biosensors, and more particularly, to a sensor that can selectively recognize and transduce the change in metal ion concentration into a measurable optical signal.

2. Description of the Related Art

Recently there has been an increasing interest in the development of practical, sensitive and miniaturized probe systems for use in monitoring metal ions such as $Ca^{2+}$, in biological media, living cells, and environmental samples. With recent advances in integrated waveguide technology and advanced photometric detection systems, fiberoptic sensors are most appropriate devices for a wide variety of monitoring applications in biological, environmental and process control applications because they shield the analytical process from the sample environment, and allow remote and in situ analysis of minute sample volumes. Fluorescence based sensors are especially useful due to their sensitivity, achieving attomole ($10^{-8}$ mole) limits of detection. Such sensors use probes that have chemical reagents or bioreceptors (such as an antibody) chemically bound to optical fibers or physically entrapped in sensing microcavities containing liquid reagents or gels attached to the distal end or to the cladding of the optical fiber. Direct attachment allows fast response time since sensor response depends on the mass transfer rate of the analyte to the immobilized reagent. In some cases, gels may be saturated with large quantities of reagent in order to enhance the sensitivity of the sensor. Physical entrapment onto the probe can also be another form of immobilization that is suitable to chemical or biological reagents. Iramobilization on cellulose or poly(vinyl chloride) films allows greater loading, but decreases response time because the reagent is immobilized in single layers.

Sensors for the detection of potassium ions are taught in U.S. Pat. No. 5,154,890 issued Oct. 15, 1992 to Mauze et al wherein 2,2-bis(3,4-(15-crown-5)- 2-nitrophenylcarbamoxymethyl)tetradecanol-14 has at least one binding site and is provided with a fluorophore such as Rhodamine-B at that binding site. The sensing material is immobilized in a gel of polyacrylamide. U.S. Pat. No. 5,176,882 issued Jan. 5, 1993 to Gray et al teaches a dual fiberoptic cell for multiple serum measurements where both a gas and an ion are analyzed simultaneously using a single probe having two separate fiber optic sensors incorporated therein. The gas is detected by the color change of a dye and the ion is detected by the fluorescing of a fluorescent metal ion sensitive dye. While this reference mentions detecting calcium the only teaching and examples are restricted to metal ions of potassium, sodium and lithium. U.S. Pat. No. 5,093,266 issued Mar. 3, 1992 to Leader et al teaches the use of a sensor probe for the determining of ptI or carbon dioxide concentration of a liquid medium using a pH-sensitive fluorescent indicator 8-hydroxy-1,3,6 -pyrenetrisulfonic acid (HPTA). Another pH sensor is disclosed in U.S. Pat. No. 5,118,405 issued Jun. 2, 1992 to Kaneko et al. U.S. Pat. No. 4,851,195 issued Jul. 25, 1989 to Matthews et al teaches another carbon dioxide sensor. Oxygen sensors and their method of use are disclosed, for example, in U.S. Pat. No. 4,974,929 issued Dec. 4, 1990 to Curry., U.S. Pat. No. 5,190,729 issued Mar. 2, 1993 and U.S. Pat. No. 4,861,727 issued Aug. 29, 1989 both to Hauenstein et al. U.S. Pat. No. 5,194,393 issued Mar. 16, 1993 to Hugl et al teaches an optical biosensor using a LB film and U.S. Pat. No. 5,227,134 issued Jul. 13, 1993 to Janata teaches a liquid/membrane cell sensor.

Many fluorescent probes have been developed to increase the usefulness of chemical sensors for non-fluorescent analytes. Sensor devices generally use chemical reagents immobilized at the terminus of an optical fiber that react with or respond to the presence of the analyte of interest. One such nonfluorescing calcium chelator used as a basis for the synthesis of some fluorescent analogues is ethyleneglycolbis($\beta$-aminoethyl ether)-N,N,N',N'-tetraacetic acid (EGTA). The first fluorescent calcium indicator was 2-{[2-[bis(carboxymethyl)amino]-5'-methylphenoxy]methyl}-6-methoxy-8-[bis(carboxymethyl)amino]quinoline (Quin-2), R. Y. Tsien, *Biochemistry*, 19, 2396 (1980). Calcium binding leads to an increase of fluorescence intensity of this compound, but its use in living cells is limited. Other types of fluorescent calcium indicators include 1H-indole-6-carboxylic acid,2-(4-bis-(carboxymethyl)amino)-3 (2-(2-(bis-carboxymethyl)amino-5-methylphenoxy)ethoxy)phenyl(Indo-1).

It is clear that there is a need for a metal ion sensor, particularly a calcium sensor, for real-time monitoring of metal ion levels in situ in a variety of situations including in vivo biological analysis and remote process control analysis.

OBJECTS AND SUMMARY OF THE INVENTION

One object of the present invention is to provide a chemical fluorescence sensor probe for metal ions.

Mother object of the present invention is to provide a chemical fluorescence sensor probe for calcium ions.

Still another object of the present invention is to provide a chemical fluorescence sensor probe for cadmium ions.

Yet another object of the present invention is to provide a device to utilize the fluorescence sensor probes of the present invention.

Yet still another object of the present invention is to provide a fiberoptic sensor probe for calcium and other metal ions.

A further object of the present invention is to provide an optical waveguide sensor probe for calcium and other metal ions.

Still a further object of the present invention is to provide a cellular biomonitor transported into the interior of cells where the transport of metal ions into and out of the cells can be monitored.

Yet another object of the invention relates to a fluorescence cellular probe for detecting the concentration of metal ions in living cells.

Yet still another object of the invention relates to a fluorescence cellular probe for detecting the concentrations of calcium or cadmium ions in living cells.

Accordingly, one form of the present invention relates to a sensor for detecting the concentration of metal ions comprising a medium consisting essentially of a gel bonded to a fluorophore, the fluorophore bonded to the gel by way of a tertiary or quaternary amine substituent containing carbodiimide.

Another, one form of the present invention relates to a sensor for detecting the concentration of calcium ions comprising a medium consisting essentially of a gel bonded to a fluorophore, the fluorophore bonded to the gel by way of a tertiary or quaternary amine substituent containing carbodiimide.

Still another form of the invention relates to a sensor for detecting the concentration of cadmium ions comprising a medium consisting essentially of a gel bonded to a fluorophore, the fluorophore bonded to the gel by way of a tertiary or quaternary amine substituent containing carbodiimide.

Yet another form of the invention relates to a detector for detecting the concentration of metal ions, said detector comprising: a source of electromagnetic radiation; a sensor comprising a medium consisting essentially of a gel bonded to a fluorophore, the fluorophore bonded to the gel by way of a tertiary or quaternary amine substituent containing carbodiimide; measuring means for measuring any change in intensity of said radiation passed through said sensor; and an optical wavelength division multiplexer for directing electromagnetic radiation from said source of electromagnetic radiation to said sensor and for detecting electromagnetic radiation from said sensor to said measuring means.

Yet still another form of the invention relates to a detector for detecting the concentration of calcium ions, said detector comprising: a source of electromagnetic radiation; a sensor comprising a medium consisting essentially of a gel bonded to a fluorophore, the fluorophore bonded to the gel by way of a tertiary or quaternary amine substituent containing carbodiimide; measuring means for measuring any change in intensity of said radiation passed through said sensor; and an optical wavelength division multiplexer for directing electromagnetic radiation from said source of electromagnetic radiation to said sensor and for detecting electromagnetic radiation from said sensor to said measuring means.

A further form of the invention relates to a detector for detecting the concentration of cadmium ions, said detector comprising: a source of electromagnetic radiation; a sensor comprising a medium consisting essentially of a gel bonded to a fluorophore, the fluorophore bonded to the gel by way of a tertiary or quaternary amine substituent containing carbodiimide; measuring means for measuring any change in intensity of said radiation passed through said sensor; and an optical wavelength division multiplexer for directing electromagnetic radiation from said source of electromagnetic radiation to said sensor and for detecting electromagnetic radiation from said sensor to said measuring means.

A still further form of the invention relates to a sensor for detecting the concentration of metal ions comprising a medium consisting essentially of a carrier moiety bonded to a fluorophore, the fluorophore bonded to the carrier moiety by way of a tertiary or quaternary amine substituent containing carbodiimide.

A further form of the invention relates to a detector for detecting the concentration of metal ions, said detector comprising: a source of electromagnetic radiation; a sensor comprising a medium consisting essentially of a carrier moiety bonded to a fluorophore, the fluorophore bonded to the carrier moiety by way of a tertiary or quaternary amine substituent containing carbodiimide; measuring means for measuring any change in intensity of said radiation passed through said sensor; and an optical wavelength division multiplexer for directing electromagnetic radiation from said source of electromagnetic radiation to said sensor and for detecting electromagnetic radiation from said sensor to said measuring means.

A still further form of the invention relates to a sensor for detecting the concentration of calcium ions comprising a medium consisting essentially of a carrier moiety bonded to a fluorophore, the fluorophore bonded to the carrier moiety by way of a tertiary or quaternary amine substituent containing carbodiimide.

Preferred forms of the invention, as well as other embodiments, objects, features and advantages of this invention, will be apparent from the following detailed description which is to be read in connection with the accompanying drawings.

DESCRIPTION OF THE PREFERRED EMBODIMENTS OF THE INVENTION

Measurement of intracellular calcium concentrations is one of the most demanding challenges of modern cellular biology. This has lead to the need to develop a calcium-sensitive probe. One method is to produce a fluorescent calcium-sensitive probe.

Figure 1:
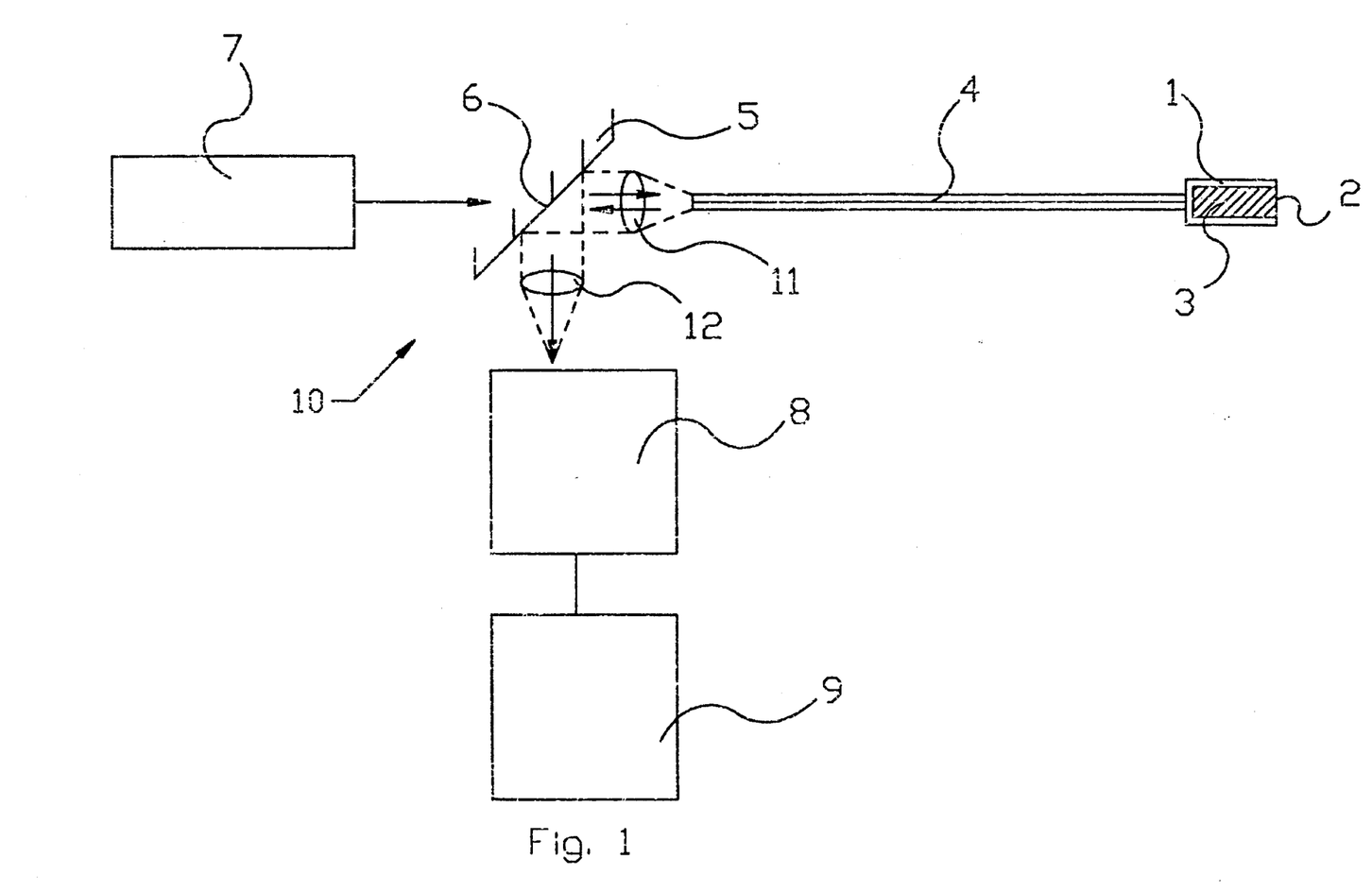
FIG. 1 shows a schematic view of one preferred embodiment of the present invention.

FIG. 1 shows a schematic representation of the metal ion sensitive probe of the present invention generally at 10 having a gel-based Indo-1 (GBI) material contained within a probe 1 having a semipermeable membrane 2. A suitable semipermeable membrane 2 is, for example, a cellulose dialysis membrane supplied by Diachem AG. The probe 1 comprises a microcavity 3, said microcavity containing the GBI material. The probe 1 is communicatively attached by a fiberoptic 4 to an excitation source 7 through a pin hole 6 in mirror 5. Pin hole 6 allows radiation from the laser excitation source 7 to travel through fiberoptic 4 and impinge on the GBI material of probe 1. The fluorescence from the sensing probe is collimated by a lens 11, reflected by mirror 5, and focused by a lens 12 into the entrance slit of a dispersive device 8 which is connected to a detector device 9. One suitable fiber optic material is a 600-μm diameter fused silica fiber available from General Fiber Optic, Inc. Other suitable fiber optic materials are well known to those skilled in the art. Laser excitation sources are also well known in the art. One suitable laser excitation source is a helium cadmium laser available as model 56X from Omnichrome, Inc. Suitable dispersive devices include, for example, monochromators and the like. One suitable dispersive device is monochromator model H10 available from Instrument SA. Detector devices suitable for use with the present invention include photomultiplier tube devices, for example. One suitable photomultiplier tube is model R760 available from Hamamatsu Corp.

Figure 2:
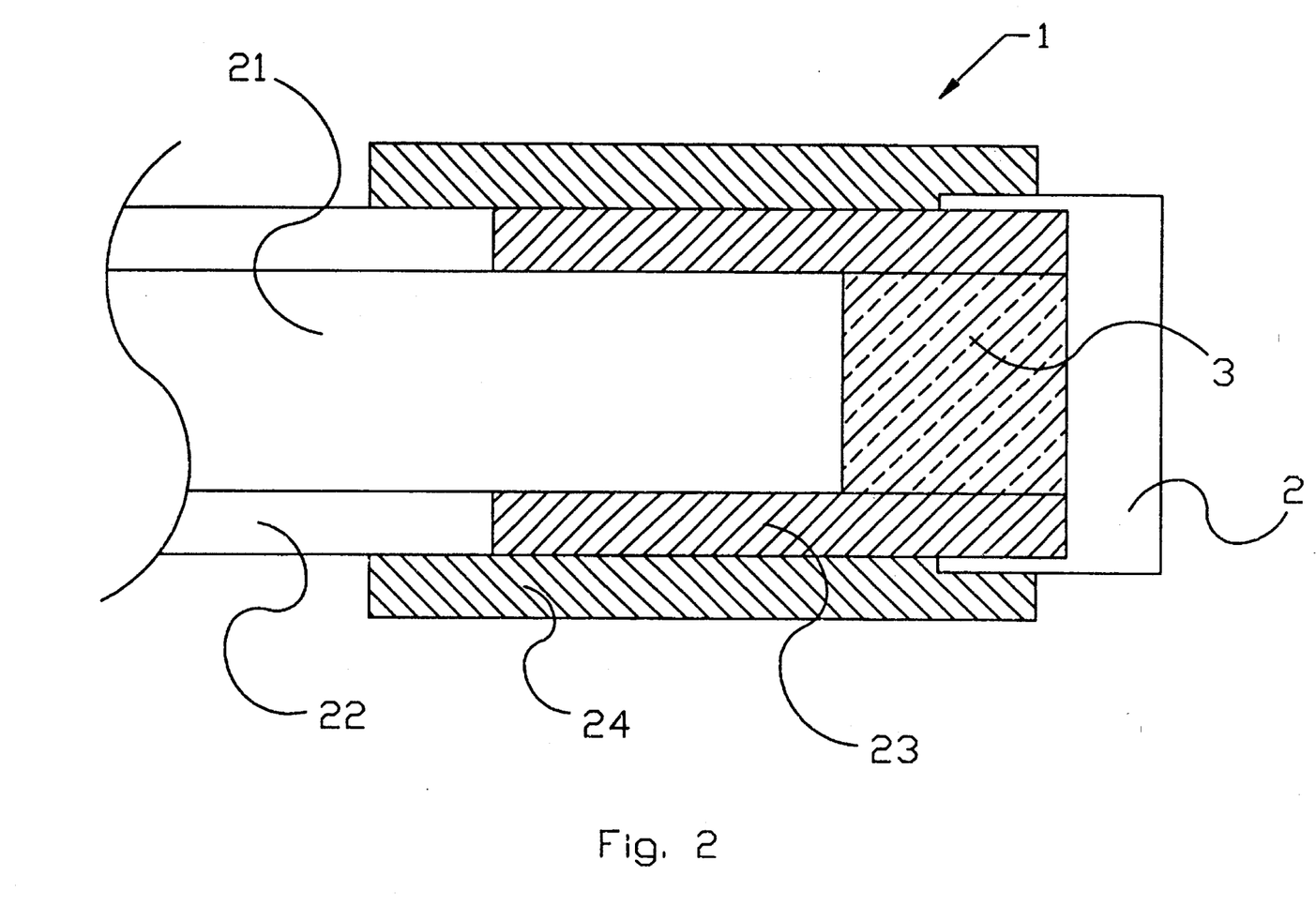
FIG. 2 shows a schematic view of one embodiment of the sensor probe of the present invention.

FIG. 2 shows a close up of the membrane sensor probe 1. The membrane sensor probe 1 is constructed with plastic-clad fused-silica fiber, having a core 21 and a cladding layer 22, for example. A cellulose dialysis membrane 2 is stretched across the face of a piece of plastic heat-shrink cylinder 23, and tightly positioned on the fiber core 21 with a band of heat-shrink tubing 24. The tip is assembled so that it can slide on and off the fiber core 21 and, when in place, a tight seal is formed between the fiber core 21 and the plastic cylinder 23. This connection is made on an approximately 2–3 mm end section of bare core 21 for example. The plastic heat-shrink cylinder 23 is tapered (not shown), resulting in a inner diameter of approximately 300-µm for the microcavity 3 which contains the GBI material. The distance between the membrane 2 and the fiber face is adjusted to 1 mm, yielding an approximate volume of 60 nanoliters for the microcavity 3.

Figure 3:
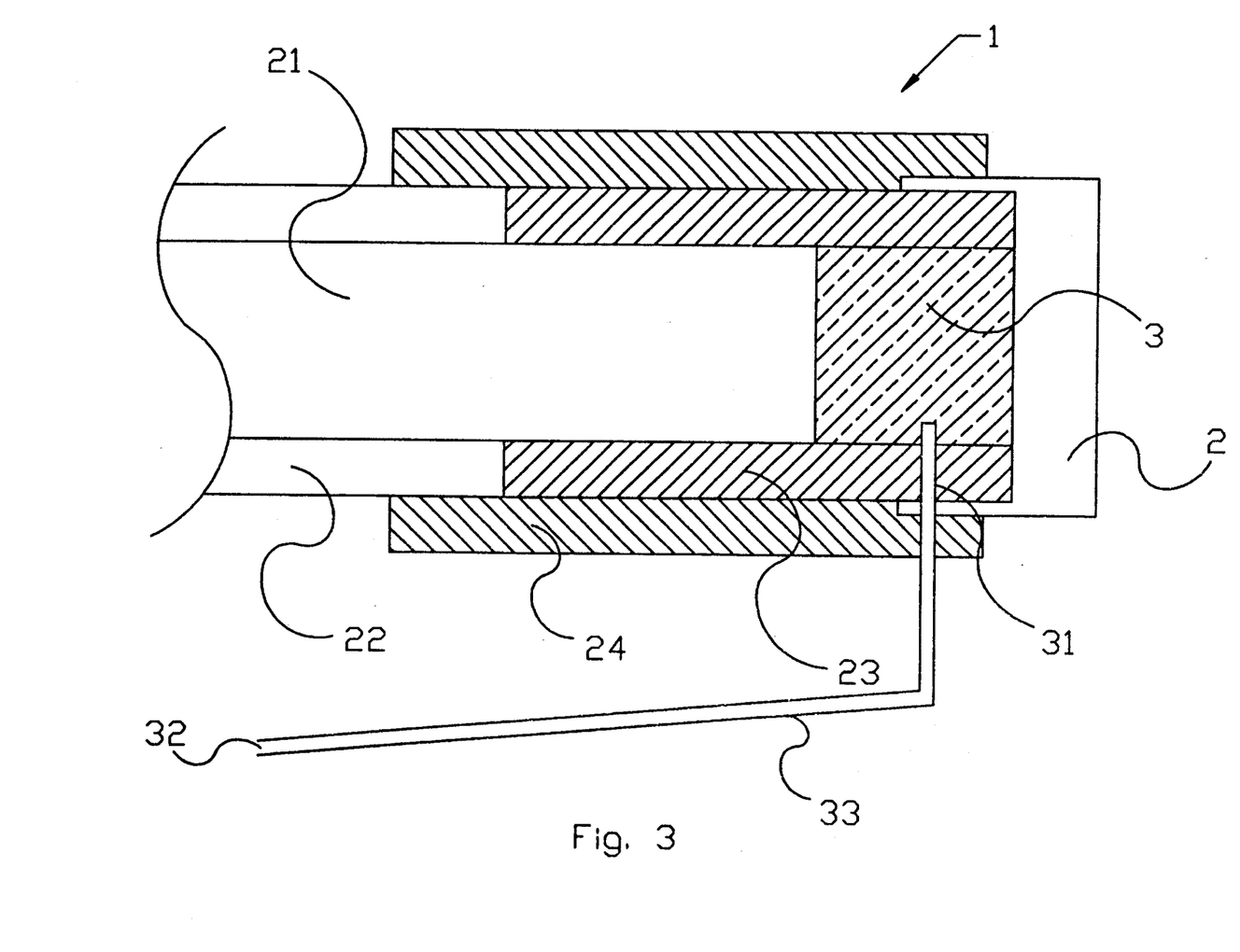
FIG. 3 shows a schematic view of a second embodiment of the sensor probe of the present invention.

FIG. 3 shows a schematic of an alternate embodiment of the membrane sensor probe 1 which has an aperture 31 to allow introduction of a phase catalyst 32 through a capillary tubing 33. The phase catalyst allows calcium ions to diffuse into the gel phase and can be used to modulate the sensitivity of the GBI probe.

Figure 4:
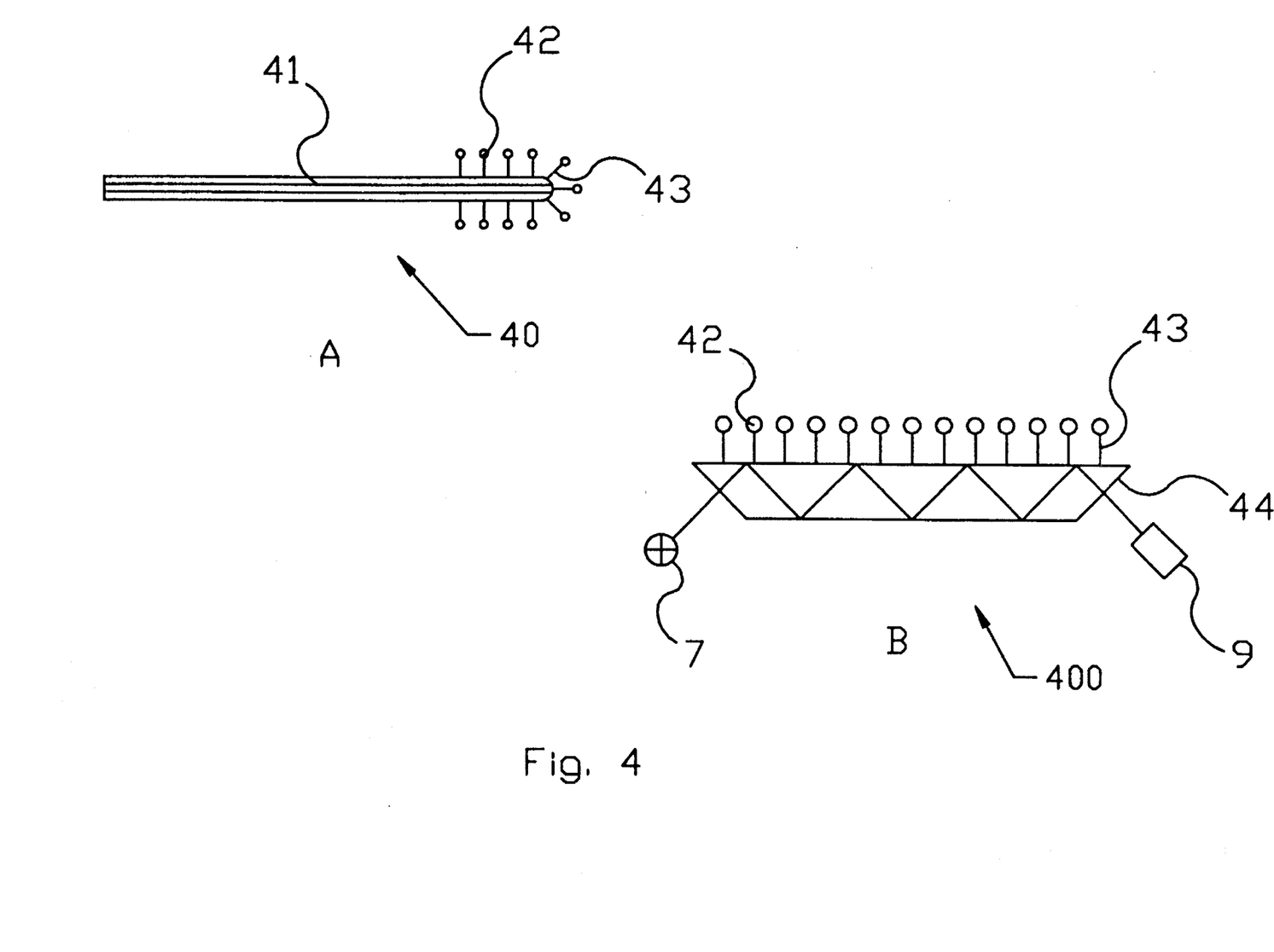
FIG. 4 shows schematic representations of two additional alternate probe configurations of the present invention.

FIG. 4A shows a fiberoptic probe 40 having an optical fiber 41 with the bound Indo-1 sensing material 42 directly attached to the fiber through a chemical bond 43.

FIG. 4B shows an optical waveguide probe 200 having a waveguide 44 with the Indo-1 sensing material 42 directly attached to the wave guide through a chemical bond 43. Also shown is excitation source 7 and detector device 9.

Figure 5:
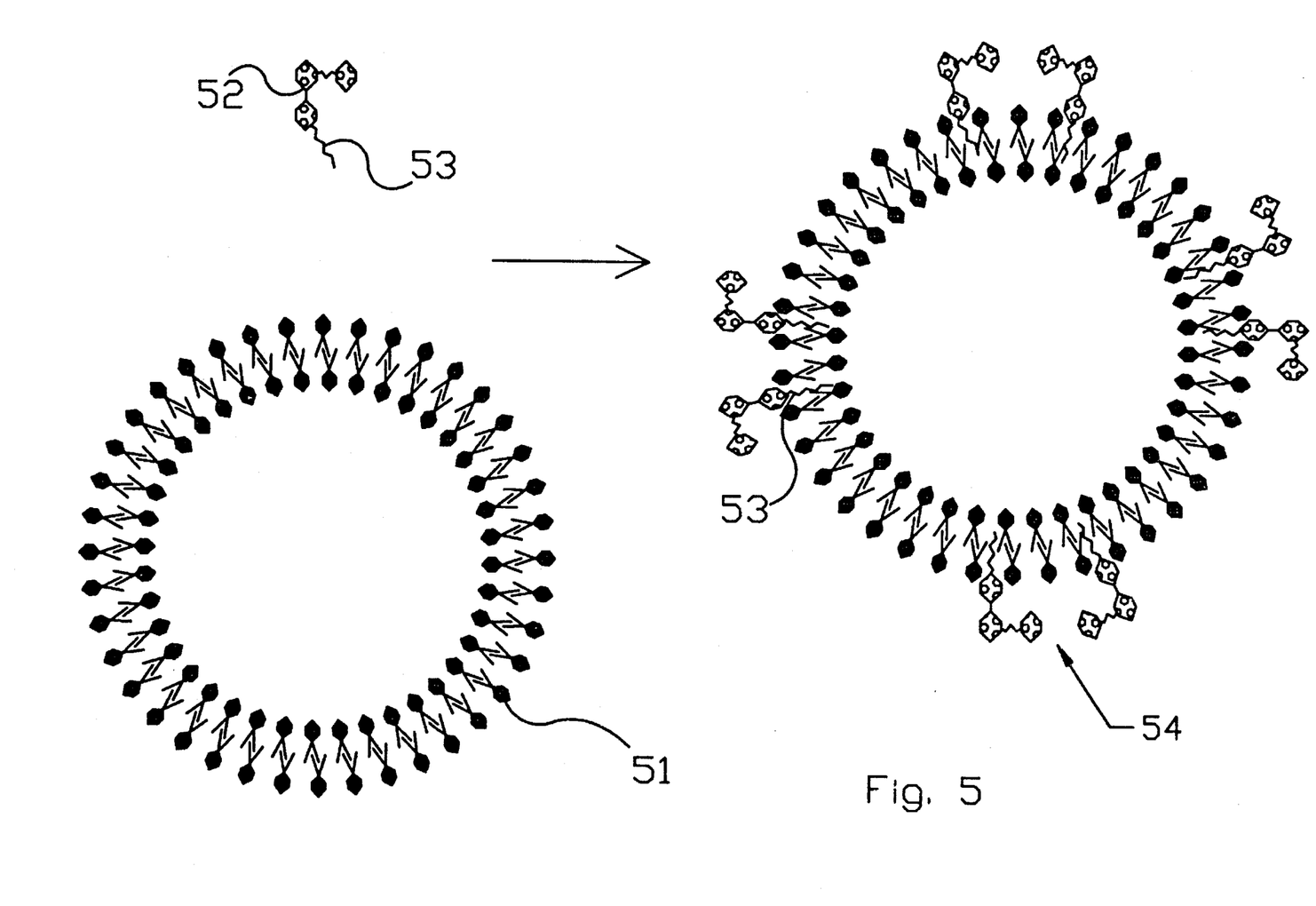
FIG. 5 shows a schematic representation of the formation of an Indo-1 liposome by way of sonication of a liposome with Indo-1 molecules.

FIG. 5 shows a schematic representation of the formation of an Indo-1 liposome 54 by way of sonication of a liposome 51 with Indo-1 molecules 52. In one example of this system the lipidic chain 53 of Indo-1 molecules 52 are embedded in the lipophilic part of the liposome. The reaction being carried out in water. The linkage between the probe and the liposome is thought to be due to lipophilic interactions. Mother approach is to covalently bond the probe to the liposome.

It is to be further understood that other ligands which can be chemically modified to contain carboxyl groups may also be used in the present invention. Thus fluorophores such as 2-{[2-[bis-(carboxymethyl)amino]-5'-methylphenoxy]methyl}-6-methoxy-8-[bis-(carboxymethyl)amino]quinoline (Quin-2) which can be chemically modified to contain carboxyl groups are also suitable for use in the present invention.

The present invention is based upon the binding of a reagent onto a gel, based on the carbodiimide procedure for formation of the amide bond, to produce gel based probes for biochemical sensors. Dicyclohexyl- and diisopropylcarbodiimide have been previously used as the coupling agents between the carboxyl and amine groups. It is noteworthy that the by-product (1,3-dicyclohexylurea) and the peptide derivatives often have similar solubility properties thus complicating the isolation procedure following the chemical reaction. The procedure of the present invention comprises using a carbodiimide containing tertiary or quaternary amine substituents because the corresponding urea derivative is soluble in dilute acid or in pure water thus facilitating its separation from the peptide derivative. A suitable, and presently preferred, coupling agent is 1-(3-dimethylaminopropyl)-3-ethyl carbodiimide hydrochloride (EDAC). EDAC may be obtained from Bio-Rad. One of the reasons this coupling agent is used is that it is a water soluble carbodiimide. While not prescribing to any one theory it is thought that the coupling reaction mechanism involves two steps, firstly activation of the carboxyl groups in order to generate a compound with a better "leaving group" and then displacement by the nucleophile group ($RNH_2$), releasing EDAC as the soluble urea derivative. This may be illustrated by wherein R is agarose—$OCH_2CONH(CH_2)_2$, $R^2$ is —$C_2H_5$, $R^3$ is —$C(CH_3)_2CH_2CH_2NH_2$, the ligand is Indo-1, and EDAC is as defined hereinabove.

One of the most important factors in producing the gel based Indo-1 (GBI) probe is the choice of a suitable gel that can serve both as an effective support and as an effective sampling medium. Amino-terminal agarose, available under the tradename Affi-Gel® 102 from Bio-Rad, is currently the preferred support gel as the host matrix for the covalent immobilization of Indo-1. This amino-terminal agarose has a structure of agarose—$OCH_2CONH(CH_2)_2NH_2$. This gel was selected due to its nonhazardous nature and because amino terminal agarose gel has a 6-atom hydrophilic spacer arm which may be illustrated as The arm provides an excellent extension from the matrix for chemical coupling requiring maximum steric freedom. The amino group concentration is 15±3 µeq/ml of settled gel bed. The gel is preferably used in a 1:1 gel/water volume ratio. The present invention selectively attaches the terminal amino group to the phenolic carboxyl group of Indo-1 using the carbodiimide coupling. The chemical structure of Indo-1 may be shown as In practice Indo-1 pentasodium salt is a suitable starting Indo-1 material and may be obtained from Molecular Probes, Inc.

Another suitable probe for use with the present invention Fura-2. Fura-2 may be utilized in place of Indo-1 and may be represented by the following chemical structure Suitable 1-[2-( 5-carboxybazole-2-yl)-6-aminobenzofuran-5-oxyl]-2(2'-amino- 5'-methylphenoxy)-ethane-N,N,N',N'-tetraacetic acid (Fura-2) includes, for example, Fura-2 supplied by Molecular Probes.

It has been found that a straight forward two step coupling reaction without any prior chemical protection of the Indo-1 carboxylic groups that will be involved in chelation with calcium resulted in all of the chelating sites of the Indo-1 molecule being blocked and therefore they were unavailable for further complexing with calcium.

As a consequence of this blocking problem, in the present invention a three step coupling reaction procedure was developed to bind the aromatic carboxyl group of Indo-1 to the amino terminal of the agarose gel. The present invention protects the carboxyl groups belonging to the chelating part of Indo-1 during the complex reaction in order to avoid any linkage between these carboxyl groups and the gel. This protection mechanism ensures the fluorescence spectrum of the resulting GBI probe exhibits the same shifts as free Indo-1 (in solution) does upon variation of the concentration of calcium ions. This procedure comprises the steps of 1) prior to binding Indo-1 to the gel, an excess of $Ca^{2+}$ is added to the Indo-1 solution thereby blocking the chelating site of Indo-1;2) once the chelating position is blocked by step 1), the covalent binding is achieved between the free carboxyl group (which does not take part in the chelation with the $Ca^{2+}$ ion of Indo-1) and the terminal amino group of the gel; and 3) after binding the Indo-1 to the gel, the chelating site of Indo-1 is unblocked by elimination of $Ca^{2+}$ in order to make it available for further complexing with the metal ions of interest.

The control of pH is important during each step of the above procedure. Step 1 is performed at $pH \geq 8$ in order to maximize the L form of the probe, the only form which is able to chelate $Ca^{2+}$ ions. For the gel/Indo-1 binding reaction of step 2 the currently preferred optimal pH is pH=6 since lower pH values (e.g., pH≈4) may induce some calcium release. This would allow for the gel/Indo-1 binding reaction to react with some of the chelating sites and reduce the usefulness of the probe. After completion of step 2, step 3 proceeds with a solution of disodium salt of ethylene diamine tetraacetic acid ($pH \geq 8$) in combination with a phase catalyst of either $N(Bu)_4^+F^-$ or $N(Bu)_4^+Cl^-$ being used in order to eliminate the $Ca^{+2}$ ions introduced in step 1.

Figure 9:
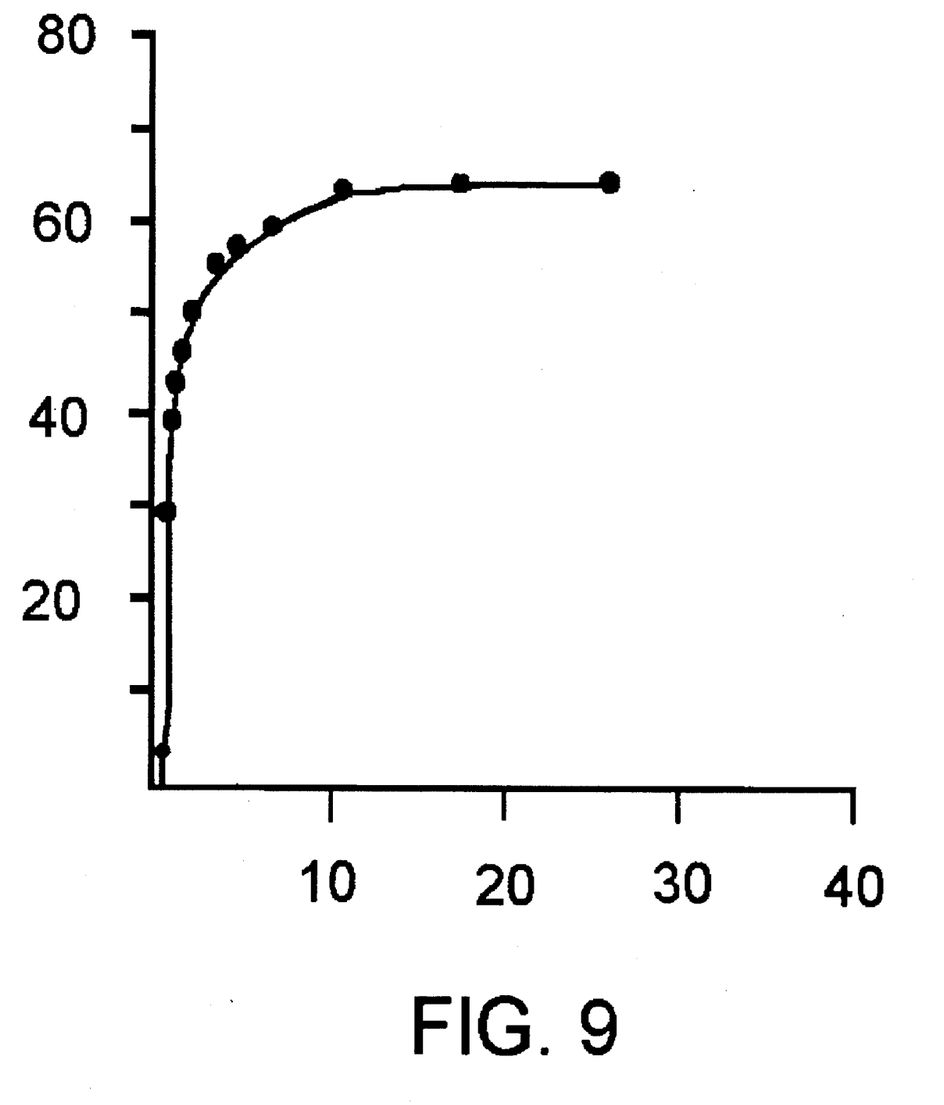
FIG. 9 is a chart showing the quantitative analytical curve of a calcium sensor probe of the present invention.

FIG. 9 shows the quantitative analytical curve of the GBI probe of the present invention for calcium is more sensitive than other probes in the art, its sensitivity is better than the free Indo-1 in solution. The Kd value which characterizes the chelation of calcium by Indo-1 in aqueous solutions has been reported to be $3 \times 10^{-6} M$, which in principle allows the determination of calcium concentrations as low as $10^{-8} M$.

Linkage of Indo-1 in the gel results in a biphasic system. This feature ensures that the molecules of Indo-1 do not react with calcium ions dissolved in the aqueous phase but only with calcium ions that are able to diffuse into the gel phase. Indeed, in the absence of any phase transfer catalyst, no interaction occurs between the gel and the calcium ions. On the other hand, addition of a phase catalyst allows these calcium ions to diffuse into the gel phase. As a consequence the sensitivity of the GBI probe (e.g., in a fiberoptic sensing device such as shown in FIG. 1) can be modulated through the concentration of the phase transfer catalyst to tune the sensitivity of the probe to various conditions and thereby match the nature of the desired biochemical analysis.

Because of the sensitivity and the non-toxic nature of the probes of the invention they may be utilized to monitor metal ion concentrations in living cells. This may be accomplished, for example, by chemically bonding the fluorophore to a carrier moiety, a liposome for example, which can carry the fluorophore directly into the living cells. The production of one such probe of the invention is illustrated in FIG. 5, wherein Indo-1 is chemically bonded to a liposome in an aqueous system through the process of sonication. This reaction is known in the art and needs no further discussion here. Once the fluorophore is chemically bound to the carrier moiety it may be transported into, and out of, living cells through the cells normal transfer system without hindrance. Examining the living cells utilizing apparatus and procedures similar to those described herein allow for the quantitative determination of the desired metal ion concentrations through fluorescence spectroscopy methods.

Another aspect of the invention relates to the use of a fluorophore such as Indo-1, Fura-2 or Quin-2 as a cellular probe. This may be accomplished by chemically bonding the fluorophore with a carrier moiety which may pass into and out of living cells. Suitable examples of such carrier moieties include liposomes, and proteins. The preferred system for chemically bonding is carried out in an aqueous system which is then compatible with living cell transport systems and mechanisms. An example of such a probe and the chemical reaction to produce it is illustrated in FIG. 5 wherein Indo-1 is chemically bound to a liposome by way of sonication, the reaction being carried out in an aqueous medium. The probe produced is then introduced into living cells where the transport of metal ions into and out of the cells may be monitored using the fluorescing characteristics described hereinabove.

The following examples are illustrative of the present invention but should not be construed as limiting the invention in any way.

EXAMPLES

In the following examples the following reagents and equipment was used:

Indo-1 pentasodium salt from Molecular Probes, Inc.

Affi-gel® 102 brand amino-terminal agarose from Bio-Rad, used in a 1:1 gel/water ratio.

EDAC coupling agent from Bio-Rad $CaCl_2$ from Fisher Co.

EGTA from Fisher Co.

Tetrabutylammonium Chloride from Aldrich Co. and used as a saturated solution.

Fluorescence experiments utilized 1 cm standard quartz cells in a Perkin-Elmer Spectrofluorometer, Model MPF-43A equipped with a R-777 photomultiplier tube and a strip-chart recorder, Model 023 from Kipp & Zonen. In all cases wavelength is measured in nanometers (nm) and the fluorescence intensity is measured in arbitrary units.

Separation of the water-gel system was accomplished using an IEC Model Centra-7R centrifuge.

EXAMPLE 1

Figure 6:
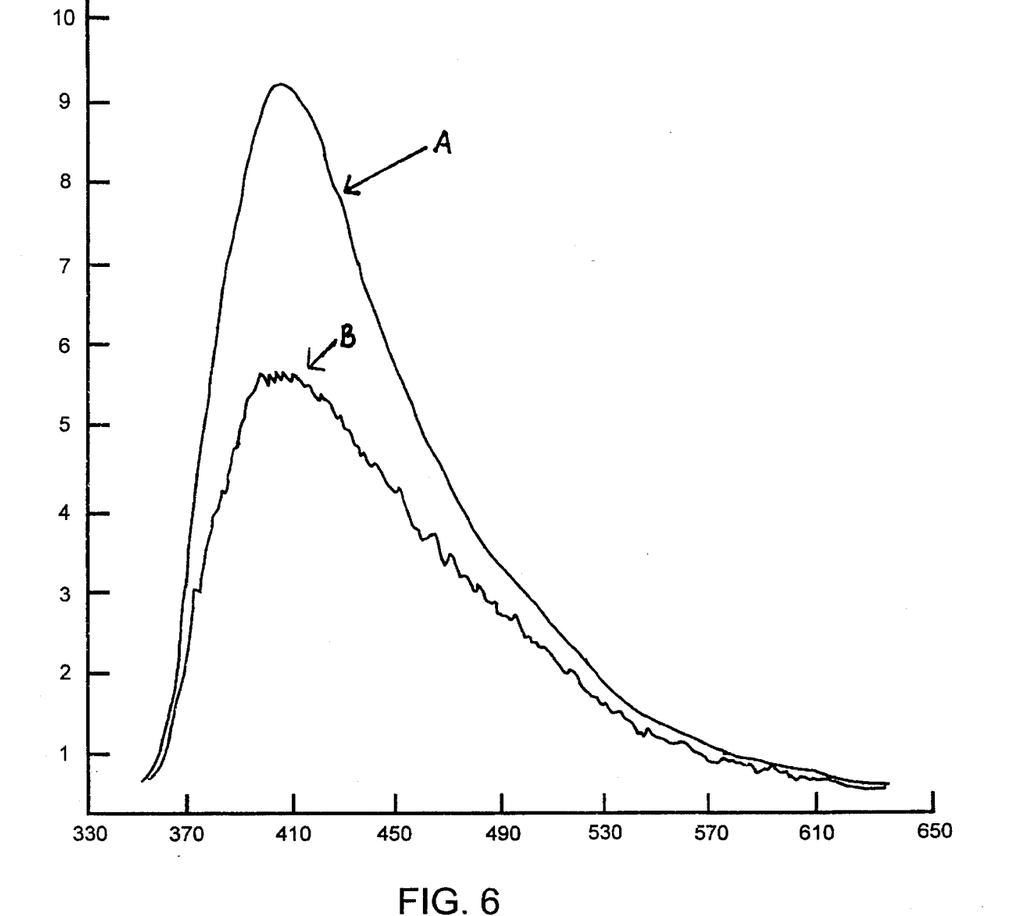
FIG. 6 is a chart showing the efficiency of the carbodiimide coupling reaction between the Indo-1/$Ca^{2+}$ ions and the gel.

Each step in the 3 step procedure was monitored by recording the fluorescence spectra ($\lambda_{ex}$=325 nm;$\lambda_{em}$=410 nm for Indo-1/$Ca^{2+}$ complex and $\lambda_{em}$ =470 nm for free Indo-1). The fluorescence spectrum of the supernatant at the end of step 2 and after centrifugation is shown in FIG. 6 as curve B. The fluorescence spectrum of the original solution of Indo-1/$Ca^{2+}$ chelate is shown in FIG. 6 as curve A. The vertical scale of curve B has been extended 3 times for better visualization of the respective peak positions. When compared to one another it was seen that the supernatant contained only 2% of the initial Indo-1/$Ca^{2+}$ complex thus demonstrating that the coupling reaction of Indo-1 to the gel was almost complete (98%) after shaking 20 hours at room temperature.

After careful washing of the gel with water in order to remove any unreacted Indo-1/$Ca^{2+}$ complexes, the fluorescence spectrum of the gel with bound Indo-1 and that of the original solution of Indo-1/$Ca^{2+}$ was compared. The results showed that fluorescence intensity of complex linked to the gel was about 80% of the free complex.

EXAMPLE 2

Figure 7:
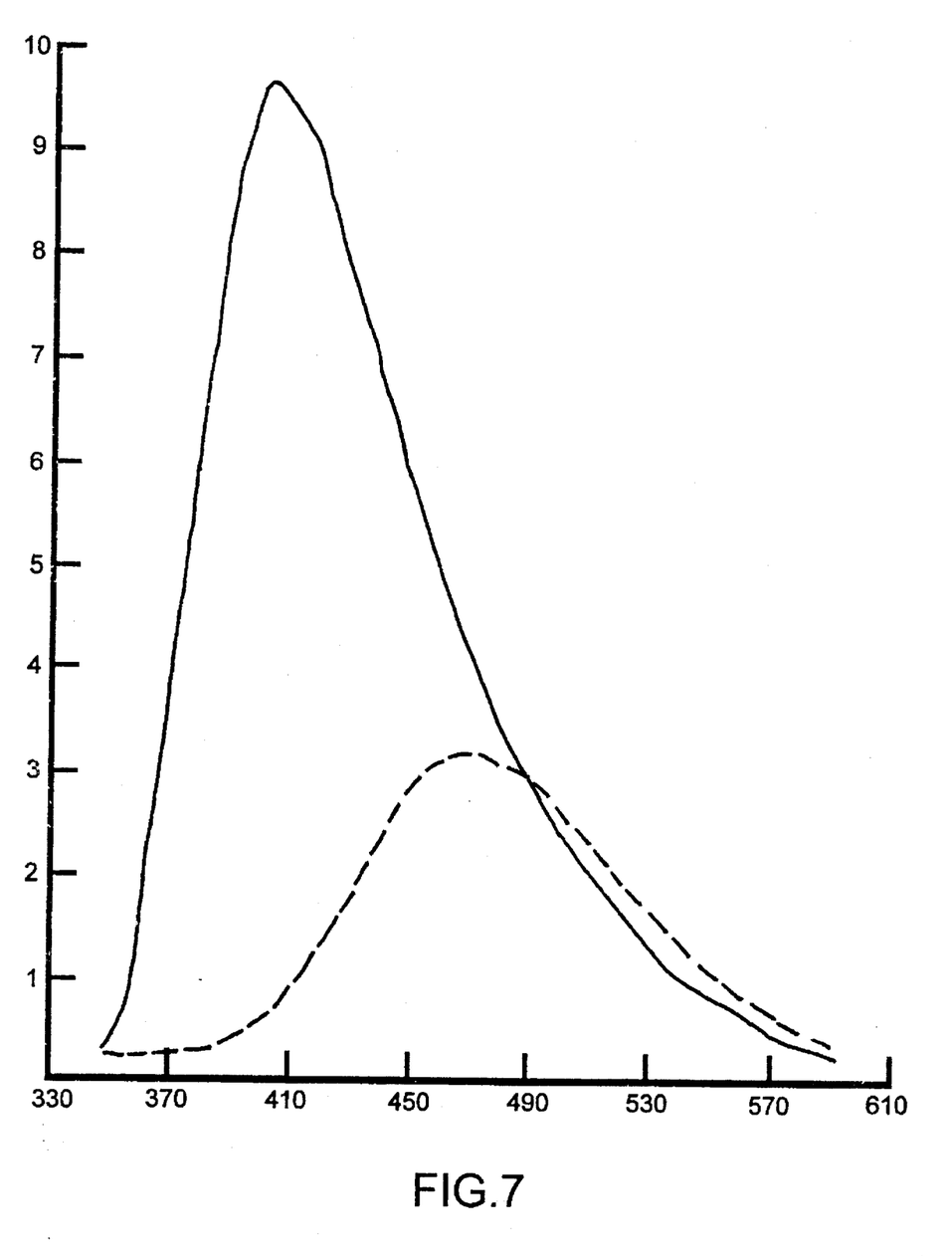
FIG. 7 is a chart showing the fluorescence spectra of a calcium sensor probe of the present invention.

To ensure that the Indo-1/gel system maintained the desired fluorescence properties to monitor the concentration of $Ca^{2+}$ in solutions fluorescence measurements were made of the Indo-1/gel system in solutions with and without $Ca^{2+}$. FIG. 7 shows the results of these fluorescence measurements. The solid line (FIG. 7) shows the Indo-1/gel which is complexed with $Ca^{2+}$ exhibiting a fluorescence maximum band at 410 nm, which is similar to that exhibited by Indo-1 in solution complexed with $Ca^{2+}$.

The $Ca^{2+}$ was then released from the Indo-1/gel system by adding an excess of disodium salt of EDTA which complexed with the $Ca^{2+}$. The resulting fluorescence spectrum of the Indo-1/gel system exhibited a fluorescence spectrum that was red-shifted by approximately 60 nm and shows a maximum band at 470 nm, the dashed line in FIG. 7.

This important result demonstrates that the Indo-1/gel system has retained the important spectral properties that are similar to that of Indo-1 in solution.

EXAMPLE 3

Figure 8:
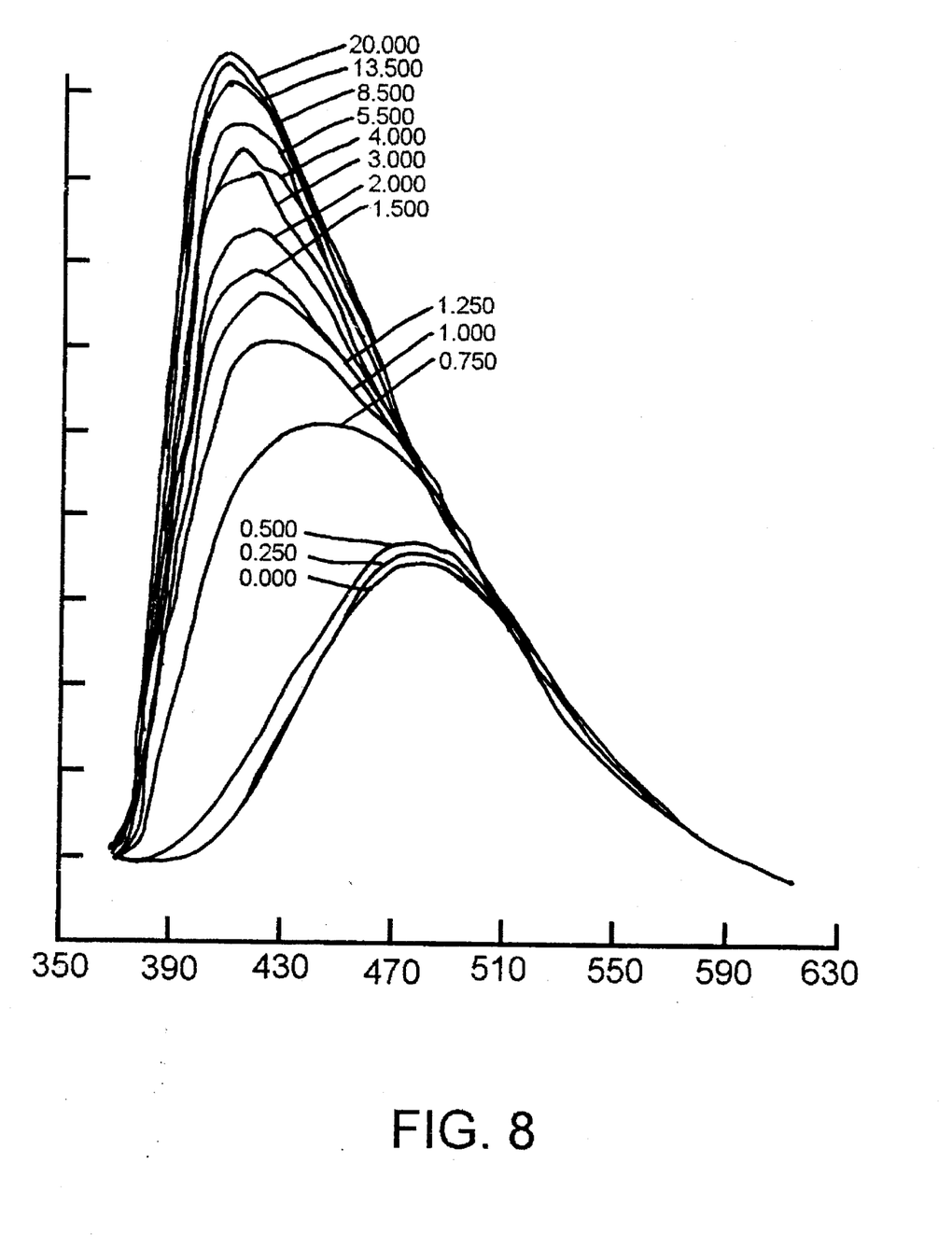
FIG. 8 is a chart showing the fluorescence spectra of a calcium sensor probe of the present invention with multiple additions of $Ca^{2+}$ ions.

The effectiveness of the Indo-1/gel probe system for quantitative determination of $Ca^{2+}$ was determined and is graphically shown in FIG. 8. FIG. 8 show the fluorescence measurement of the probe exposed to increasing amounts of $Ca^{2+}$ ions. The fluorescence spectra of FIG. 8 were obtained by adding $CaCl_2$ solution ($1.0 \times 10^{-2}$M) in small increments into the gel probe. The results showed the gradual increase in fluorescence intensity ($\lambda_{ex}$=325 nm; $\lambda_{em}$=410 nm) and the blue shift of the spectrum as the amount of $Ca^{2+}$ increased. The sensitivity (limit of optical detection=$3 \times 10^{-6}$M, estimated with the signal-to-noise ration=3) of the present invention is 100-fold better than previously known and can be easily adapted to analyze real-life biological samples ($\sim 10^{-3}$M).

The analytical curve showing fluorescence intensity versus concentration of $Ca^{2+}$ ($10^{-5}$M) is shown in FIG. 9.

EXAMPLE 4

Figure 10:
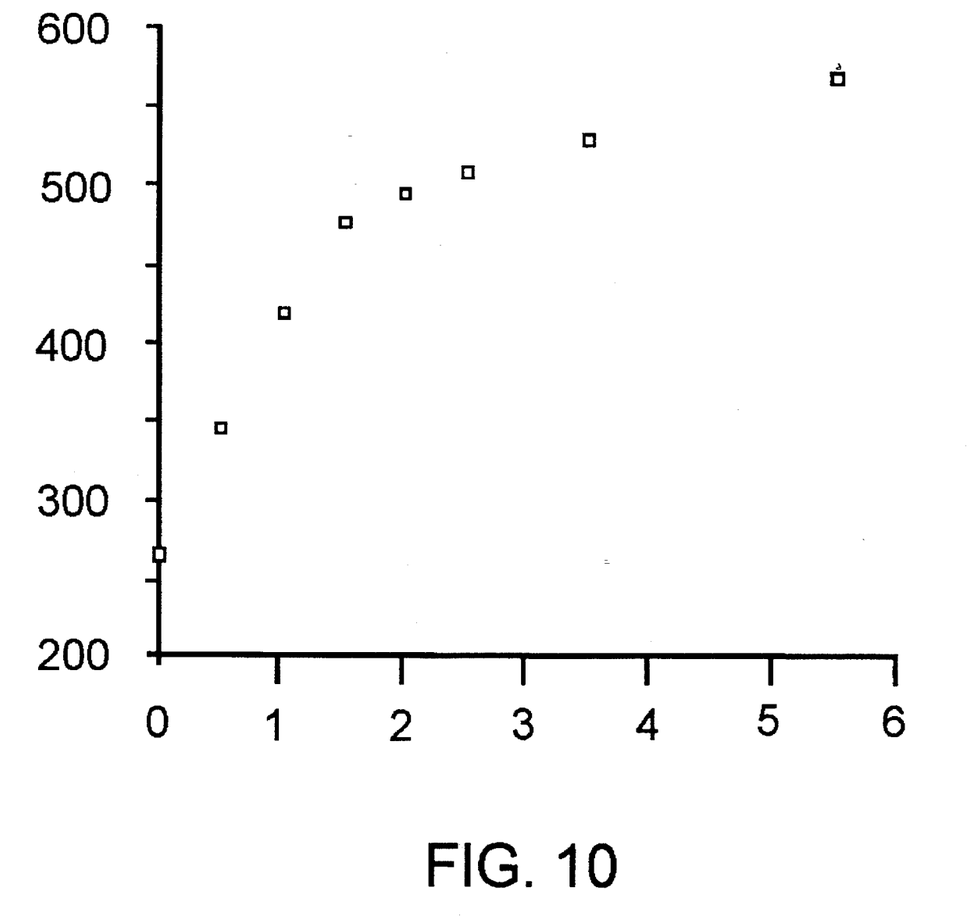
FIG. 10 is a chart showing the quantitative analytical curve of a cadmium sensor probe of the present invention.

The effectiveness of the Indo-1/gel probe system for quantitative determination of $Cd^{2+}$ was determined and is graphically shown in FIG. 10. Here the analytical curve showing intensity, in arbitrary units, versus concentration of $CdCl_2$ ($10^{-7}$M) exhibits a $Cd^{+2}$ ion concentration curve similar to that found for $Ca^{2+}$.

Although the illustrative embodiments of the present invention have been described herein with reference to the above experiments and the accompanying drawings it is to be understood that the invention is not limited to those precise embodiments, and that various other changes and modifications may be effected therein by one skilled in the art without departing from the scope or spirit of the invention.

What is claimed is:

1. A sensor for detecting the concentration of metal ions comprising a medium consisting essentially of a gel bonded to a fluorophore, the fluorophore bonded to the gel by way of a carbodiimide comprising 1-(3-dimethylaminopropyl)-3-ethyl carbodiimide hydrochloride.

2. A sensor for detecting the concentration of calcium ions comprising a medium consisting essentially of a gel bonded to a fluorophore, the fluorophore bonded to the gel by way of a carbodiimide comprising 1-(3-dimethylaminopropyl)-3-ethyl carbodiimide hydrochloride.

3. A sensor for detecting the concentration of cadmium ions comprising a medium consisting essentially of a gel bonded to a fluorophore, the fluorophore bonded to the gel by way of a carbodiimide comprising 1-(3-dimethylaminopropyl)-3-ethyl carbodiimide hydrochloride.

* * * * *